US009173733B1

(12) United States Patent
Lim et al.

(10) Patent No.: US 9,173,733 B1
(45) Date of Patent: Nov. 3, 2015

(54) TRACHEOBRONCHIAL IMPLANTABLE MEDICAL DEVICE AND METHODS OF USE

(75) Inventors: Florencia Lim, Union City, CA (US); Mary Suh, Evanston, IL (US); Barbara Stamberg, San Jose, CA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 740 days.

(21) Appl. No.: 11/507,913

(22) Filed: Aug. 21, 2006

(51) Int. Cl.
| | | |
|---|---|---|
| *A61F 2/20* | (2006.01) | |
| *A61F 2/04* | (2013.01) | |
| *A61F 2/18* | (2006.01) | |

(52) U.S. Cl.
CPC . *A61F 2/04* (2013.01); *A61F 2/186* (2013.01); *A61F 2002/043* (2013.01); *A61F 2002/046* (2013.01); *A61F 2210/0004* (2013.01); *A61F 2230/0091* (2013.01); *A61F 2250/0015* (2013.01); *A61F 2250/0018* (2013.01); *A61F 2250/0028* (2013.01)

(58) Field of Classification Search
CPC .............................................. A61F 2250/0028
USPC ........ 623/1.1, 1.12, 1.15, 1.2, 1.3, 1.42, 1.46, 623/9, 1.22
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |

(Continued)

FOREIGN PATENT DOCUMENTS

| | | |
|---|---|---|
| DE | 44 07 079 | 9/1994 |
| DE | 197 31 021 | 1/1999 |

(Continued)

OTHER PUBLICATIONS

Anonymous, "Bioabsorbable stent mounted on a catheter having optical coherence tomography capabilities," Research Disclosure, Sep. 2004, pp. 1159-1162.

(Continued)

*Primary Examiner* — Thomas J Sweet
*Assistant Examiner* — Rebecca Preston
(74) *Attorney, Agent, or Firm* — Randy Shen, Esq.; Blakely Sokoloff Taylor & Zafman LLP

(57) ABSTRACT

Devices and methods for treating a diseased tracheobronchial region in a mammal. The device can be a stent which can include a sustained-release material such as a polymer matrix with a treatment agent. The stent can be bioabsorbable and a treatment agent can be incorporated therewith. A treatment method can be delivery of a stent to a tracheobronchial region by a delivery device such as a catheter assembly.

17 Claims, 5 Drawing Sheets

(56) References Cited

U.S. PATENT DOCUMENTS

| | | |
|---|---|---|
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,760,849 A * | 8/1988 | Kropf .................... 606/191 |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,575,818 A * | 11/1996 | Pinchuk .................... 623/1.15 |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |

(56) References Cited

U.S. PATENT DOCUMENTS

| | | |
|---|---|---|
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,455 A | 1/2000 | Barnett et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,814,754 B2 * | 11/2004 | Greenhalgh .................. 623/1.51 |
| 6,818,063 B1 | 11/2004 | Kerrigan |
| 6,846,323 B2 | 1/2005 | Yip et al. |
| 6,997,946 B2 | 2/2006 | Girton et al. |
| 7,582,108 B2 * | 9/2009 | Hierlemann et al. ......... 623/1.15 |
| 2001/0029398 A1 | 10/2001 | Jadhav |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0082682 A1 * | 6/2002 | Barclay et al. ............... 623/1.22 |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0004563 A1 | 1/2003 | Jackson et al. |
| 2003/0033001 A1 | 2/2003 | Igaki |
| 2003/0069629 A1 | 4/2003 | Jadhav et al. |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0170287 A1 * | 9/2003 | Prescott ........................ 424/423 |
| 2003/0171053 A1 | 9/2003 | Sanders |
| 2003/0187495 A1 | 10/2003 | Cully et al. |
| 2003/0208256 A1 | 11/2003 | DiMatteo et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | Fiter |
| 2004/0093077 A1 | 5/2004 | White et al. |
| 2004/0098095 A1 | 5/2004 | Burnside et al. |
| 2004/0111149 A1 | 6/2004 | Stinson |
| 2004/0116958 A1 * | 6/2004 | Gopferich et al. ............ 606/199 |
| 2004/0127970 A1 | 7/2004 | Weber |
| 2004/0143317 A1 | 7/2004 | Stinson et al. |

(56) References Cited

U.S. PATENT DOCUMENTS

| | | | |
|---|---|---|---|
| 2004/0167610 A1 | 8/2004 | Fleming, III | |
| 2005/0021131 A1* | 1/2005 | Venkatraman et al. | 623/1.19 |
| 2005/0049694 A1* | 3/2005 | Neary | 623/1.46 |
| 2005/0137678 A1 | 6/2005 | Varma | |
| 2005/0149172 A1 | 7/2005 | Varma | |
| 2005/0177246 A1* | 8/2005 | Datta et al. | 623/23.7 |
| 2005/0240147 A1* | 10/2005 | Makower et al. | 604/96.01 |
| 2005/0245906 A1* | 11/2005 | Makower et al. | 604/891.1 |
| 2006/0018948 A1* | 1/2006 | Guire et al. | 424/426 |
| 2006/0041102 A1 | 2/2006 | Hossainy et al. | |
| 2006/0070626 A1* | 4/2006 | Frazier et al. | 128/207.14 |

FOREIGN PATENT DOCUMENTS

| | | |
|---|---|---|
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Ansari, "Tubal Reanastomosis Using Absorbable Stent," *International Journal of Fertility*, vol. 23, No. 4, pp. 242-243 (1978).
Ansari, "End-to-end tubal anastomosis using an absorbable stent," *Fertility and Sterility*, vol. 32(2), pp. 197-201 (Aug. 1979).
Casper et al., "Fiber-Reinforced Absorbable Composite for Orthopedic Surgery," *Polymeric Materials Science and Engineering*, vol. 53, pp. 497-501 (1985).
Detweiler et al., "Gastrointestinal Sutureless Anastomosis Using Fibrin Glue: Reinforcement of the Sliding Absorbable Inraluminal Nontoxic Stent and Development of a Stent Placement Device," *Journal of Investigative Surgery*, vol. 9(2), pp. 111-130 (Mar./Apr. 1996).
Detweiler et al., "Sliding, Absorbable, Reinforced Ring and an Axially Driven Stent Placement Device for Sutureless Fibrin Glue Gastrointestinal Anastomisis," *Journal of Investigative Surgery*, vol. 9(6), pp. 495-504 (Nov./Dec. 1996j.
Detweiler et al., "Sutureless Anastomosis of the Small Intestine and the Colon in Pigs Using an Absorbable Intraluminal Stent and Fibrin Glue," *Journal of Investigative Surgery*, vol. 8(2), pp. 129-140 (Mar. 1995).
Detweiler et al., "Sutureless Cholecystojejunostomy in Pigs Using an Absorbable Intraluminal Stent and Fibrin Glue," *Journal of Investigative Surgery*, vol. 9(1), pp. 13-26 (Jan./Feb. 1996).

Devanathan et al., "Polymeriic Conformal Coatings for Implantable Electronic Devices," *IEEE Transactions on Biomedical Engineering*, vol. BME-27(11), pp. 671-675 (1980).
Elbert et al., "Conjugate Addition Reactions Combined with Free-Radical Cross-Linking for the Design of Materials for Tissue Engineering," *Biomacromolecules 2*, pp. 430-441 (2001).
Feng-Chun et al., "Assessment of Tissue Blood Flow Following Small Artery Welding with an Intraluminal Dissolvable Stent," *Microsurgery*, vol. 19(3), pp. 148-152 (1999).
Hahn et al., "Blocompatibility of Glow-Discharge-Polymerized Films and Vacuum-Deposited Parylene," *J Applied Polymer Sci*, vol. 38, pp. 55-64 (1984).
Hahn et al., "Glow Discharge Polymers as Coatings for Implanted Devices," *ISA*, pp. 109-111 (1981).
Hossainy et al., "Biocompatible coating for implantable medical devices," U.S. Appl. No. 10/317,435, filed Dec. 11, 2002.
Kelley et al., "Totally Resorbable High-Strength Composite Material," *Advances in Biomedical Polymers*, vol. 35, pp. 75-85 (1987).
Kubies et al., "Microdomain Structure in polylactide-block-poly(ethylene oxide) copolymer films," *Biomaterials*, vol. 21, pp. 529-536 (2000).
Kutryk at al., "Coronary Stenting: Current Perspectives," a companion to the *Handbook of Coronary Stents*, pp. i-16 (1999).
Martin et al., "Enhancing the biological activity of immobilized osteopontin using a type-1 collagen affinity coating," *J. Biomed. Mater. Res.*, vol. 70A, pp. 10-19 (2004).
Mauduit at al., "Hydrolytic degradation of films prepared from blends of high and low molecular weight poly(DL-lactic acid)s," J. Blamed. Mater. Res., vol. 30, pp. 201-207 (1996).
McClay, "Laryngeal and Tracheal Stents," *Emedicine*, (Aug. 18, 2004). Mar. 21, 2006: <http://www.emedicine.com/ent/topic593htm>.
Middleton et al., "Synthetic biodegradable polymers as orthopedic devices," *Biomaterials*, vol. 21, pp. 2335-2346 (2000).
Muller at al., "Advances in Coronary Angioplasty: Endovascular Stents," *Caron. Arter. Dis.*, vol. 1(4), pp. 438-448 (Jul./Aug. 1990).
Nichols et al., "Electrical Insulation of Implantable Devices by Composite Polymer Coatings," *ISA Transactions*, vol. 26(4), pp. 15-18 (1987).
Peuster et al., "A novel approach to temporary stenting: degradable cardiovascular stents produced from corrodible metal-results 6-18 months after implantation into New Zealand white rabbits," *Heart*, vol. 86, pp. 563-569 (2001).
Pietrzak et al., "Bioresorbable implants—practical considerations," *Bone*, vol. 19, No. 1, suppl., pp. 109S-119S (Jul. 1996).
Pietrzak at al., "Bioabsorbable Fixation Devices: Status for the Craniomaxillofacial Surgeon," *J. Craniofaxial Surg.*, vol. 2, pp. 92-96 (1997).
von Recum et al., "Degradation of polydispersed poly(L-lactic acid) to modulate lactic acid release," *Biomaterials*, vol. 16, pp. 441-445 (1995).
Redman, "Clinical Experience with Vasovasostomy Utilizing Absorbable Intravasal Stent," *Urology*, vol. 20(1), pp. 59-61 (Jul. 1982).
Rust et al., "The Effect of Absorbable Stenting on Postoperative Stenosis of the Surgically Enlarged Maxillary Sinus Ostia in a Rabbit Animal Model," *Archives of Otolaryngology*, vol. 122(12), pp. 1395-1397 (Dec. 1996).
Schatz, "A View of Vascular Stents," *Circulation*, vol. 79(2), pp. 445-457 (Feb. 1989).
Schmidt et al., "Long-Term Implants of Parylene-C Coated Microelectrodes," *Med & Blot Eng & Comp*, vol. 26(1), pp. 96-101 (Jan. 1988).
Spagnuoio et al., "Gas 1 is induced by VE-cadherin and vascular endothelial growth factor and inhibits endothelial cell apoptosis," *Blood*, vol. 103, pp. 3005-3012 (2004).
Tamai et al., "Initial and 6-Month Results of Biodegradable Poly-I-Lactic Acid Coronary Stents in Humans," *Circulation*, pp. 399-404 (2000).
Tsuji et al., "Biodegradable Polymeric Stents," *Current Interventional Cardiology Reports*, vol. 3, pp. 10-17 (2001).
Volker at al., "Targeting of immunoliposomes to endothelial cells using a single-chain Fv fragment directed against human endoglin (CD105)," *Biochemica et Blophysica Acta*, 1663, pp. 158-166 (2004).

\* cited by examiner

TRACHEOBRONCHIAL IMPLANTABLE MEDICAL DEVICE AND METHODS OF USE

FIELD OF INVENTION

Bioabsorbable implantable medical devices for the treatment of lesions caused by cancer of the tracheobronchial tree or cancer of the head, neck or chest.

BACKGROUND OF INVENTION

This invention relates generally to radially expandable endoprostheses which are adapted to be implanted in a physiological lumen. An "endoprosthesis" corresponds to an artificial device that is placed inside of a physiological lumen. A "lumen" refers to a cavity of a tubular organ such as a blood vessel or other physiological passageway. A stent, or implantable medical device, is an example of an endoprosthesis. Stents are generally cylindrically shaped devices which function to hold open or expand a physiological lumen, or to compress a lesion. A stent must be able to satisfy a number of mechanical requirements. For example, the stent must be capable of withstanding the structural loads, namely radial compressive forces, imposed on the stent as it supports the walls of the tubular organ. Accordingly, a stent must possess adequate radial strength.

In adults, primary cancer of the tracheobronchial tree or cancer of the head, neck or chest that extends into the tracheobronchial tree frequently causes lumen compromise and airway obstruction. "Tracheobronchial" refers to the physiological passageway from the throat to the lungs. In some methods of treatment, a compromised component of the tracheobronchial tree can be removed by laser treatment, mechanical debulking, electrocautery, brachytherapy, photodynamic therapy or cryotherapy. A stent can then be placed at the treatment site following removal of a comprised component to maintain the airway lumen to counteract collapse or edema.

Alternatively, a stent can be placed to help compress any lesion extending into the tracheo or bronchi without the need for removal of the compromised component. In some methods of treatment, a stent has been used to palliate patients with inoperable bronchogenic cancer, primary tracheal tumors and metastatic malignancies.

Stents which have been used in the tracheobronchial tree include metal, silicone and bioabsorbable stents. Metallic stents are generally made from an inert metal such as stainless steel, cobalt chromium and Nitinol. Some problems associated with known stent types delivered to the tracheobronchial region include inflammation, stent migration, epithelial damage, granulation tissue formation and mucous plugging. In addition, it is believed that known bioabsorbable stents designed for placement in the tracheobronchial region are not able to adequately combat inflammation caused by stent placement.

"Stent migration" refers to the gradual movement of the stent down the tracheobronchial tree after placement thereof. Stent migration of silicone stents in the tracheobronchial tree is common. "Mucous plugging" is an excessive production of mucous produced in response to the stent. Mucous plugging can cause interference with breathing. "Granulation tissue formation" is the formation of new tissue in response to a wound or other disruption of tissue. Excessive granulation tissue formation can cause a stent to be permanently lodged within a passageway complicating removal if required. Metal stents are especially susceptible to granulation tissue formation. Accordingly, a tracheobronchial stent which addresses these problems is desirable.

SUMMARY OF INVENTION

Devices and methods for treating a diseased tracheobronchial region in a mammal are herein disclosed. The device can be a stent which can include a sustained-release material such as a polymer matrix with a treatment agent. The stent can be a bioabsorbable stent and a treatment agent can be incorporated therewith. A treatment method can be delivery of a stent to a tracheobronchial region by a delivery device such as a catheter assembly.

DETAILED DESCRIPTION

Embodiments of devices and methods for treating a diseased tracheobronchial region in a mammal, including, but not limited to, humans, are herein disclosed. In some embodiments, the device can be an implantable medical device such as a stent. Representative examples of implantable medical devices include, but are not limited to, self-expandable stents, balloon-expandable stents, micro-depot or micro-channel stents and grafts. In some embodiments, a treatment method can be delivery of a stent to a tracheobronchial region by a delivery device such as a catheter assembly.

In some treatment applications, a stent may only be required to be present in the tracheobronchial region for a limited period of time. To accommodate this, a stent can be made of a biodegradable, bioerodable or bioabsorbable polymer, hereinafter used interchangeably. A stent can also be made of a biostable or biodurable (hereinafter used interchangeably) or a combination of a biostable and biodegradable polymer. A stent made from a biodegradable polymer is intended to remain in the body for a duration of time until its intended function of, for example, maintaining luminal patency and/or drug delivery, is accomplished. After the process of degradation, erosion, absorption and/or resorption has been completed, none or substantially none of the biodegradable portion of the stent will remain in the tracheobronchial region.

In some embodiments, the stent may include a treatment agent. As used herein, treatment agents are intended to include, but are not intended to be limited to, drugs, biologically active agents, chemically active agents, therapeutic agents, and the like, and pharmaceutical compositions thereof, which can be used to deliver a treatment agent to a treatment site as described herein. Representative treatment agents include, but are not limited to, an anti-inflammatory, an anti-platelet, an anti-coagulant, a fibrinolytic, an anti-thrombonic, an anti-mitotic, an anti-biotic, an anti-allergic, an anti-oxidant, an anti-proliferative and an anti-migratory. The treatment agent may be incorporated within the body of the stent or within a polymer-based coating applied on or within the stent.

Tracheobronchial Stents

Figure 1:
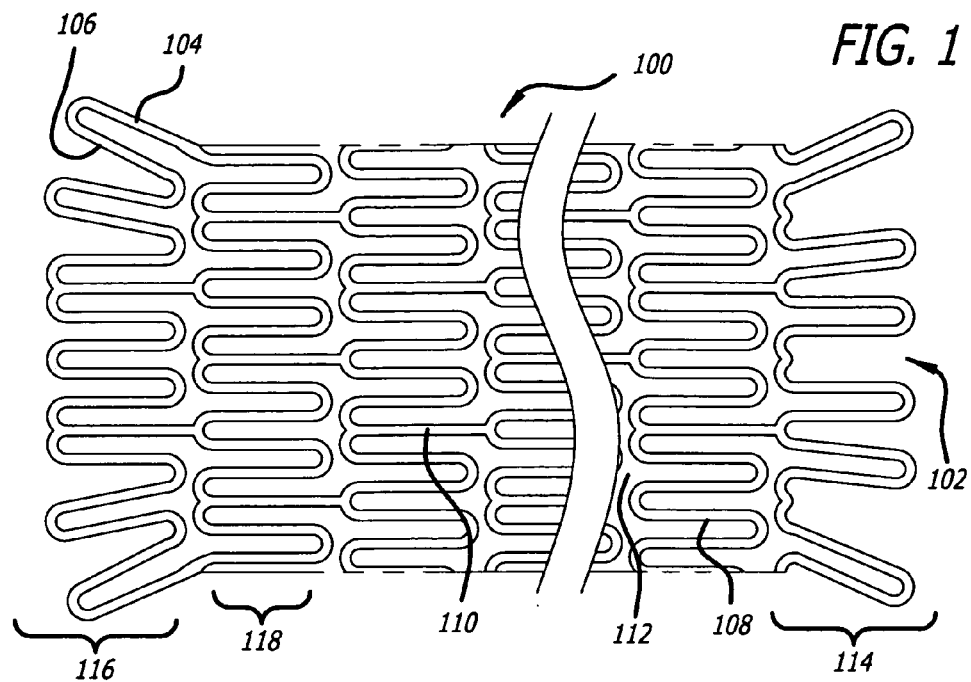
FIG. 1 illustrates a side view of an embodiment of a stent of the present invention.

FIG. 1 illustrates an embodiment of a stent. Stent 100 is generally tubular and includes a lumen 102 with an abluminal surface 104 and a luminal surface 106. Stent 100 can include a plurality of struts 108 connected by linking struts 110 with interstitial spaces 112 located therebetween. The plurality of struts 108 can be configured in an annular fashion in discrete "rows" such that they form a series of "rings" throughout the body of stent 100. Thus, stent 100 can include a proximal ring 114, i.e., proximal concentric end region, distal ring 116, i.e., distal concentric end region, and at least one central ring 118, i.e., middle concentric region. In some embodiments, proximal ring 114 and distal ring 116 can have a larger outer diameter than that of central rings 118. For example, the outer diameter (OD) of central rings 118 can be from about 3.5 mm to about 25 mm, and in some embodiments, from about 8 to about 20 mm. The OD of proximal ring 114 and distal ring 116 can be from about 5.0 mm to about 30 mm, and in some embodiments, from about 10 to about 22 mm. Such configuration may reduce or eliminate stent migration.

Figure 2:
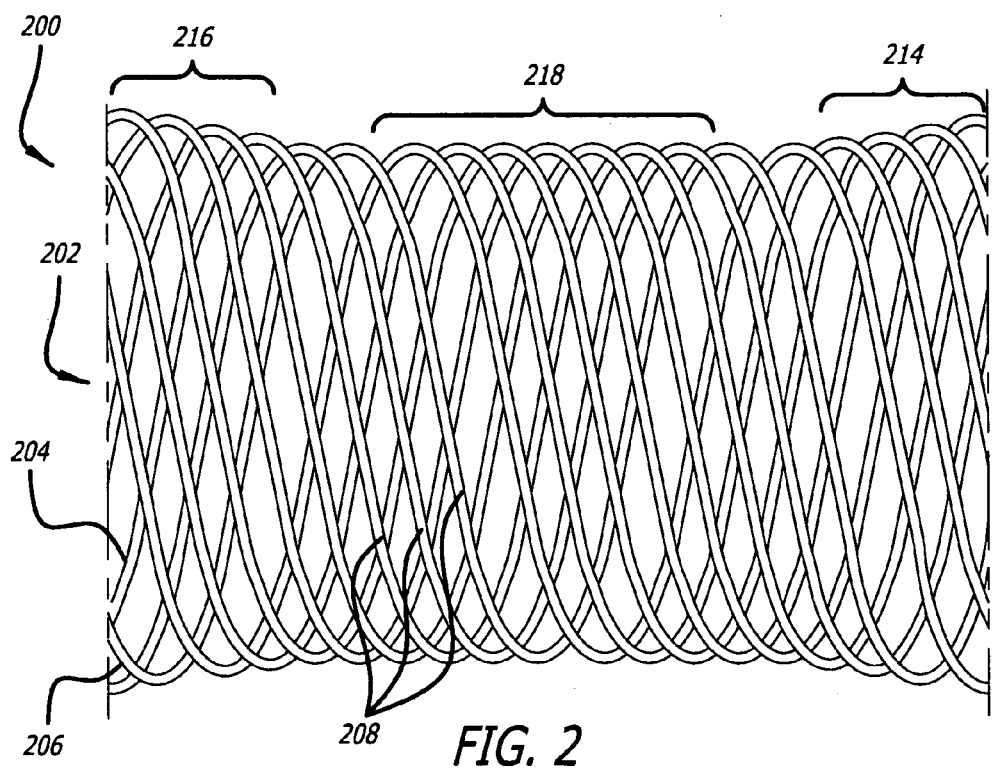
FIG. 2 illustrates a side view of an alternative embodiment of a stent of the present invention.

FIG. 2 illustrates an alternative embodiment of a stent. Stent 200 is generally tubular and includes a lumen 202 with an abluminal surface 204 and a luminal surface 206. Stent 200 can include a series of filaments 208 which can be interconnected in a braided, twisted or coiled fashion. Filaments 208 may be fabricated from a biodurable or biodegradable metal or polymer. Tubular stent 200 can include a proximal end 214, a distal end 216 and at least one central portion 218. In some embodiments, proximal end 214 and distal end 216 can have a larger outer diameter than that of central portion 218 similar to those ranges given with respect to FIG. 1. Stent 200 can be a self-expanding stent.

Figure 3A:
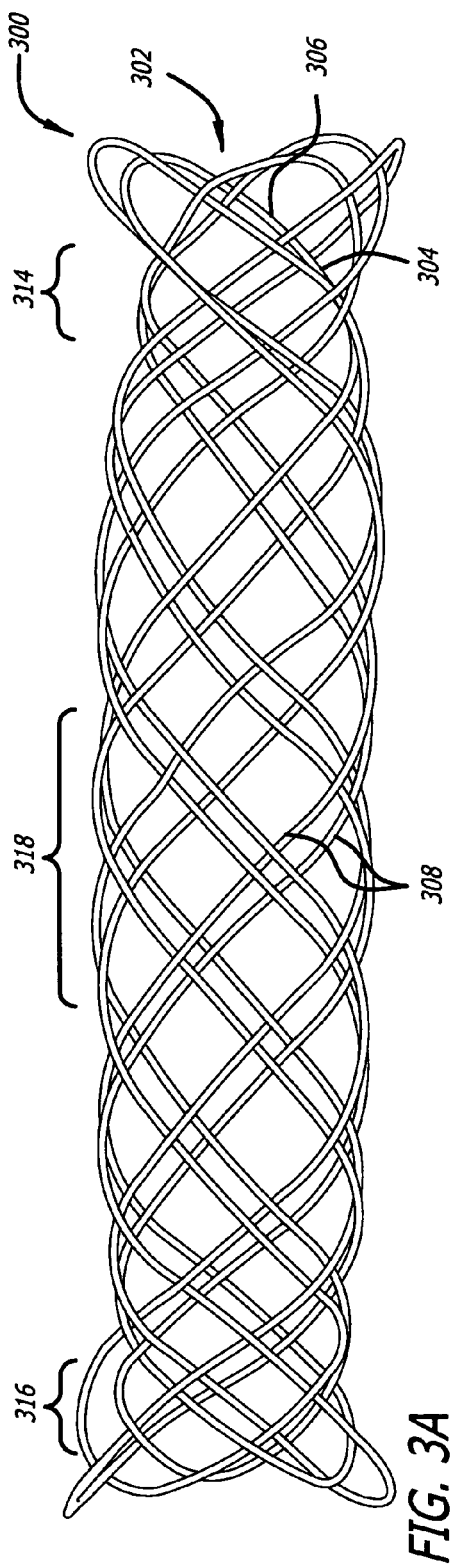
FIG. 3A illustrates side view of a first alternative embodiment of a stent of the present invention.

FIG. 3A illustrates another alternative embodiment of a stent. Stent 300 is generally tubular and includes a lumen 302 with an abluminal surface 304 and a luminal surface 306. Stent 300 can include a series of filaments 308 which can be interconnected in a braided, twisted, weaved or coiled fashion. Filaments 308 may be fabricated from a biodurable or biodegradable metal or polymer. Tubular stent 300 can include a proximal end 314, a distal end 316 and at least one central portion 318. In some embodiments, proximal end 314 and distal end 316 can have a larger outer diameter than that of central portion 318 similar to those ranges given with respect to FIG. 1. Stent 300 can be a self-expanding stent.

Figure 3B:
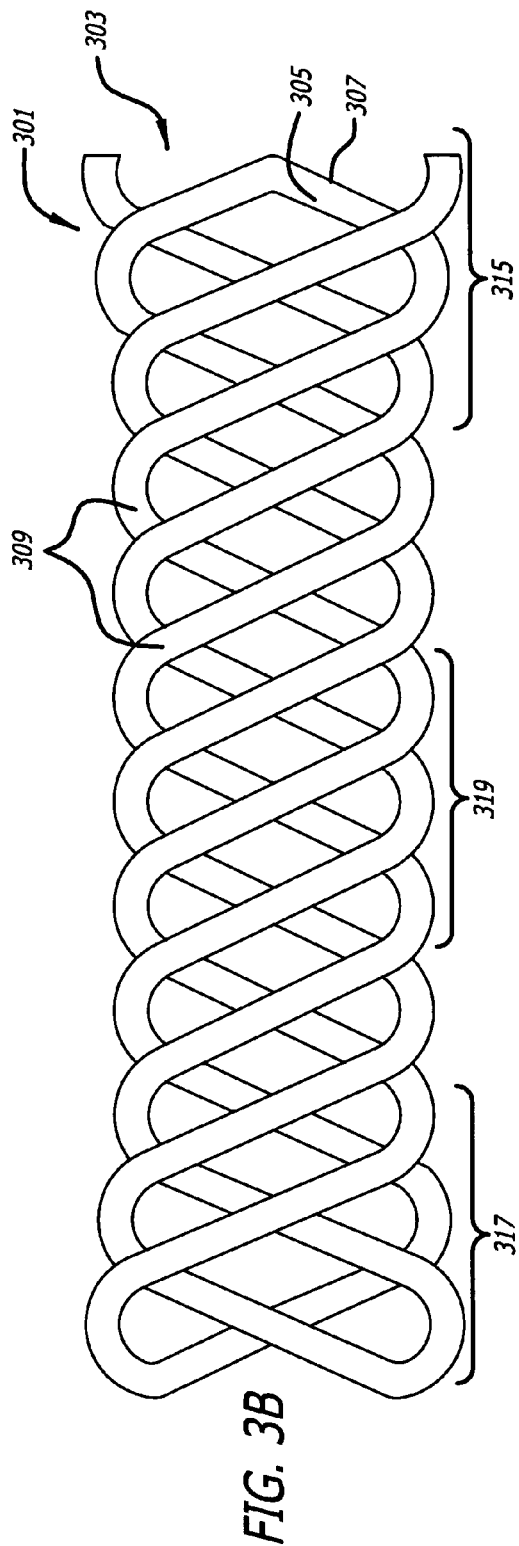
FIG. 3B illustrates side view of a second alternative embodiment of a stent of the present invention.

FIG. 3B illustrates another alternative embodiment of a stent. Stent 301 is generally tubular and includes a lumen 303 with an abluminal surface 305 and a luminal surface 307. Stent 301 can include a series of filaments 309 which can be interconnected in a braided, twisted, weaved or coiled. Filaments 309 may be fabricated from a biodurable or biodegradable metal or polymer. Tubular stent 301 can include a proximal end 315, a distal end 317 and at least one central portion 319 similar to those ranges given with respect to FIG. 1. In some embodiments, proximal end 315 and distal end 317 can have a larger outer diameter than that of central portion 319. Stent 301 can be a self-expanding stent.

In some embodiments, a stent according to the present invention can have variable radial strength along the stent length. For example, the stent can have higher radial strength at the proximal and distal ends relative to the central portions. In this aspect, the higher radial strength proximal and distal ends can serve as "anchors" after placement in the tracheobronchial tree. It is anticipated that higher radial strength proximal and distal ends can substantially minimize, or even prevent, stent migration.

Figure 3C:
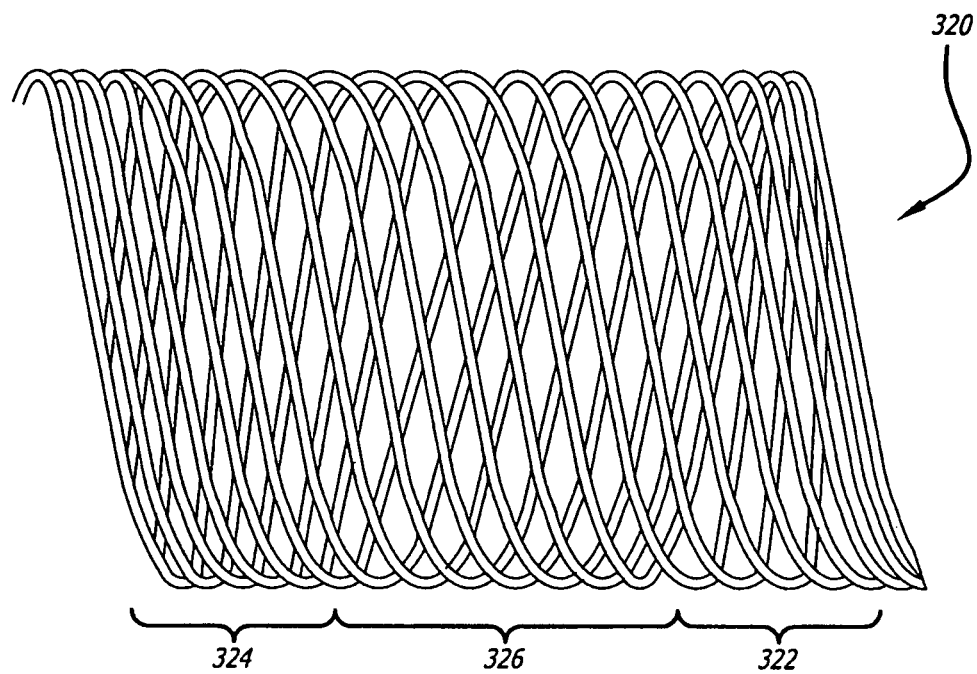
FIG. 3C illustrates an embodiment of a braided stent with variable radial strength.

FIG. 3C illustrates an embodiment of a braided stent with variable radial strength. Stent 320 includes proximal end 322, distal end 324 and at least one central portion 326. Proximal end 322 and distal end 324 can have higher picks per inch, or pitch (hereinafter referred to interchangeably), which can give ends 322 and 324 higher radial strength relative to central portion 326. "Pitch" is the density of material in a given unit of length. In some embodiments, a thin polymer fiber can be extruded, drawn and heat set to the dimensions ranging from about 0.003 inches to about 0.010 inches. The fibers can be wound onto a bobbin or spool and braided into a stent using a braiding machine. Braiding machines for stent fabrication are generally known by those skilled in the art. The pitch for central portion 326 of stent 320 can be predetermined by using the appropriate gear dimension in the braiding machine in the braiding machine to produce a predetermined picks per inch. Once central portion of stent 320 has been braided, the gear dimension in the braiding machine can be changed to accommodate fabrication of higher picks per inch of proximal end 322 and distal end 324. In some embodiments, central portion 326 can have a pitch of about 40 to about 90 picks per inch while ends 322 and 324 can have a pitch from about 60 to about 100 picks per inch. In any case, the proximal and distal ends will have higher picks per inch as compared to the central portion. In some embodiments, ends 322 and 324 can be from about 1.0 mm to about 5.0 mm. After braiding, stent 320 can be heat set. For example, in braided stents comprised of poly-L-lactic acid, heat setting can be done at between about 120° C. to about 160° C. for about 10 to about 30 minutes.

Figure 3D:
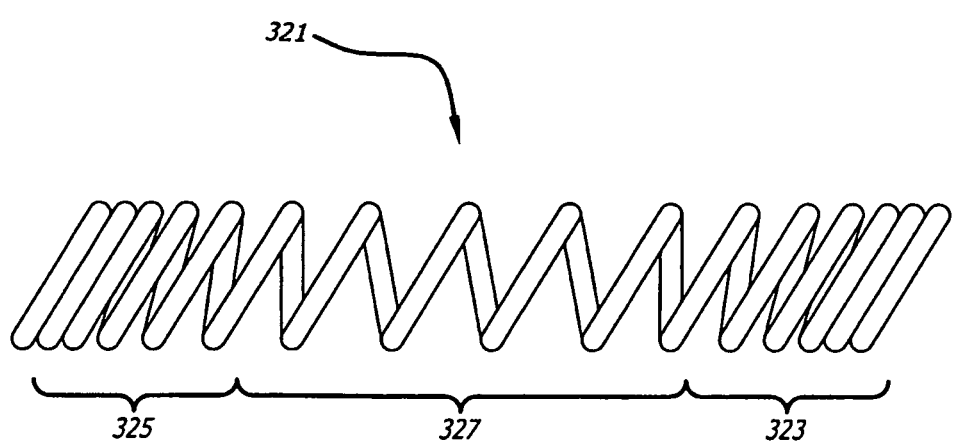
FIG. 3D illustrates an embodiment of a coiled stent with variable radial strength.

FIG. 3D illustrates an embodiment of a coiled stent with variable radial strength. Stent 321 includes proximal end 323, distal end 325 and at least one central portion 327. Proximal end 323 and distal end 325 can have a higher pitch angle, which can give ends 323 and 325 higher radial strength relative to central portion 327. "Pitch angle" is defined as the angle between the direction of the fiber and longitudinal axis. In some embodiments, a thin polymer fiber can be extruded, drawn and heat set to the dimensions ranging from about 0.003 inches to about 0.010 inches. The fiber can be coiled onto a mandrel with a predetermined pitch angle for central portion 327. Proximal end 323 and distal end 325 can be constructed using a higher pitch angle to increase radial strength. In some embodiments, central portion 327 can have a pitch angle of about 25° to about 70°, while ends 323 and 325 can have a pitch angle from about 50° to about 90°. In any case, the pitch angle at the proximal and distal ends will be higher than the central portion for increased radial strength. In some embodiments, ends 323 and 325 can be from about 1.0 mm to about 10.0 mm. After coiling, stent 321 can be heat set. For example, in coiled stents comprised of poly-L-lactic acid, heat setting can be done at between about 120° C. to about 160° C. for about 10 to about 30 minutes.

In general, a stent is designed so that the stent can be radially compressed (crimped) and radially expanded (to allow deployment). The stresses involved during compression and expansion are generally distributed throughout various structural elements of the stent. As a stent deforms, various portions of the stent can deform to accomplish radial expansion. In this aspect, the stent must be sufficiently malleable to withstand compression and expansion.

On the other hand, the stent must exhibit a certain degree of rigidity to maintain lumen patency during its lifetime. For a bioabsorbable stent, a lifetime can be from about 2 months to about 24 months depending on the intended application. Thus, a biodegradable stent is preferably fabricated from a polymer which allows for sufficient malleability during compression and expansion, and sufficient rigidity after deployment thereof.

Representative examples of polymers that may be used to manufacture or coat a stent, include but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic), poly(caprolactone), poly(trimethylene carbonate), polyester amide, poly(glycolic acid-co-trimethylene carbonate), co-poly(etheresters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile styrene copolymers, ABS resins, polyamides (such as Nylon 66 and polycaprolactam), polycarbonates, polyoxymethylenes, polyimides, polyethers, polyurethanes, rayon, rayon-tracetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in manufacturing or coating stents include ethylene vinyl alcohol copolymer (e.g., EVOH or EVAL), poly(butyl methacrylate), poly(vinylidene fluoride-co-hexfluorapropene (e.g., SOLEF 21508, available from Solvay Solexis PVDF, Thorofare, N.J.), polyvinylidene fluoride (e.g., KYNAR, available from ATOFINA Chemicals, Philadelphia, Pa.), ethylene-vinyl acetate copolymers and polyethylene glycol.

Manufacturing processes for forming a bioabsorbable stent include, but are not limited to, casting, molding, extrusion, drawing or combinations thereof. Casting involves pouring a liquid polymeric composition into a mold. Molding processes include, but are not limited to, compression molding, extrusion molding, injection molding and foam molding. In compressing molding, solid polymeric materials are added to a mold and pressure and heat are applied until the polymeric material conforms to the mold. In extrusion molding, solid polymeric materials are added to a continuous melt that is forced through a die and cooled to a solid form. In injection molding, solid polymeric materials are added to a heated cylinder, softened and forced into a mold under pressure to create a solid form. In foam molding, blowing agents are used to expand and mold solid polymeric materials into a desired form, and the solid polymeric materials can be expanded to a volume in a range from about 2 to about 50 times their original volume. In the above-described molding embodiments, the solid form may require additional processing to obtain the final product in a desired form. Additional processing may include fiber processing methods such as hot drawing to induce orientation and higher crystallinity for increased mechanical strength.

The material for the stent can also be produced from known man-made fiber processing methods such as dry spinning, wet spinning, and melt spinning. In dry spinning, a polymer solution in warm solvent is forced through a tiny hole into warm air. The solvent evaporates into the air and the liquid stream solidifies into a continuous filament. Wet spinning method involves a polymer solution forced through tiny holes into another solution where it is coagulated into a continuous filament. Melt spinning method is a method in which a solid polymer is melted and forced through a tiny hole into cool air which solidifies the fiber into a continuous filament.

In some embodiments, a stent may be fabricated from a biocompatible metal or metal alloy. Representative examples include, but are not limited to, stainless steel (316L or 300), MP35N, MP2ON, Nitinol, Egiloy, tantalum, tantalum alloy, cobalt-chromium alloy, nickel-titanium alloy, platinum, iridium, platinum-iridium alloy, gold, magnesium or combinations thereof. MP35N and MP2ON are trade names for alloys of cobalt, nickel, chromium and molybdenum available from Standard Press Steel Co., Jenkintown, Pa. MP35N consists of 35 percent (%), cobalt, 35% nickel, 20% chromium and 10% molybdenum. MP2ON consists of 50% cobalt, 20% nickel, 20% chromium and 10% molybdenum.

In some embodiments, a treatment agent may be directly incorporated into the body of a bioabsorbable stent during the manufacturing process. For example, a treatment agent may be combined with a polymer matrix and subsequently subjected to any of the above-described manufacturing process for formation thereof. In this aspect, the treatment agent may be released in a controlled manner as the bioabsorbable stent naturally degrades in the tracheobronchial region.

In some applications, a polymer coating comprising at least one layer including a treatment agent can be applied to a surface of a stent for controlled release of the treatment agent. The polymer can be a polymer which exhibits a sustained-release characteristic of the treatment agent. For example, the polymer can be polyglycolide (PGA) which has a degradation rate of about 9 months to about 12 months. In another example, the polymer can be polylactide (PLA) which has a degradation rate of about 14 and about 18 months. Copolymers of PLA and PGA can also be used to tailor degradation rates. It should be appreciated that more than one coating may be applied to treat a variety of symptoms typically experienced with tracheobronchial stent placement.

For example, a coating can include one or a combination of the following types of layers: (a) a treatment agent layer, which may include a polymer and a treatment agent, or alternatively, a polymer-free treatment agent; (b) an optional primer layer, which may improve adhesion of subsequent layers on the stent or on a previously formed layer; (c) an optional topcoat layer, which may serve to control the rate of release of the treatment agent; and (d) an optional biocompatible finishing layer, which may improve the biocompatibility of the coating.

In some embodiments, the coating can be partially or completely applied to an abluminal surface or a luminal surface of the stent. The coating can be applied by methods known by those skilled in the art, including, but not limited to, dipping, spraying, pouring, brushing, spin-coating, roller coating, meniscus coating, powder coating, drop-on-demand coating, sputtering, gas-phase polymerization, solvent inversion or any combination thereof. Coating techniques are known by those skilled in the art.

The coating which includes a treatment agent can include, but is not limited to, an anti-inflammatory, an anti-platelet, an anti-coagulant, a fibrinolytic, an anti-thrombonic, an anti-mitotic, an anti-biotic, an anti-allergic, an anti-oxidant, an anti-proliferative and an anti-migratory. In some embodiments, the treatment agent can be an anti-inflammatory steroid or non-steroid. Examples of anti-inflammatory steroids include, but are not limited to, prednisone, oxymetholone, oxandrolone and methanodrostenolone. Examples of anti-inflammatory non-steroids (NSAID) include, but are not limited to, ibuprofen, diclofenac, diflunisal, fenoprofen, aspirin, sulindac, naproxen, indomethacin, piroxicam, ketoprofen, tolmetin and azapropazonelast.

The treatment agent can treat symptoms typically associated with tracheobronchial stent deployment, such as, inflammation, epithelial damage, granulation tissue formation and mucous plugging.

Methods of Delivery

Figure 4A:
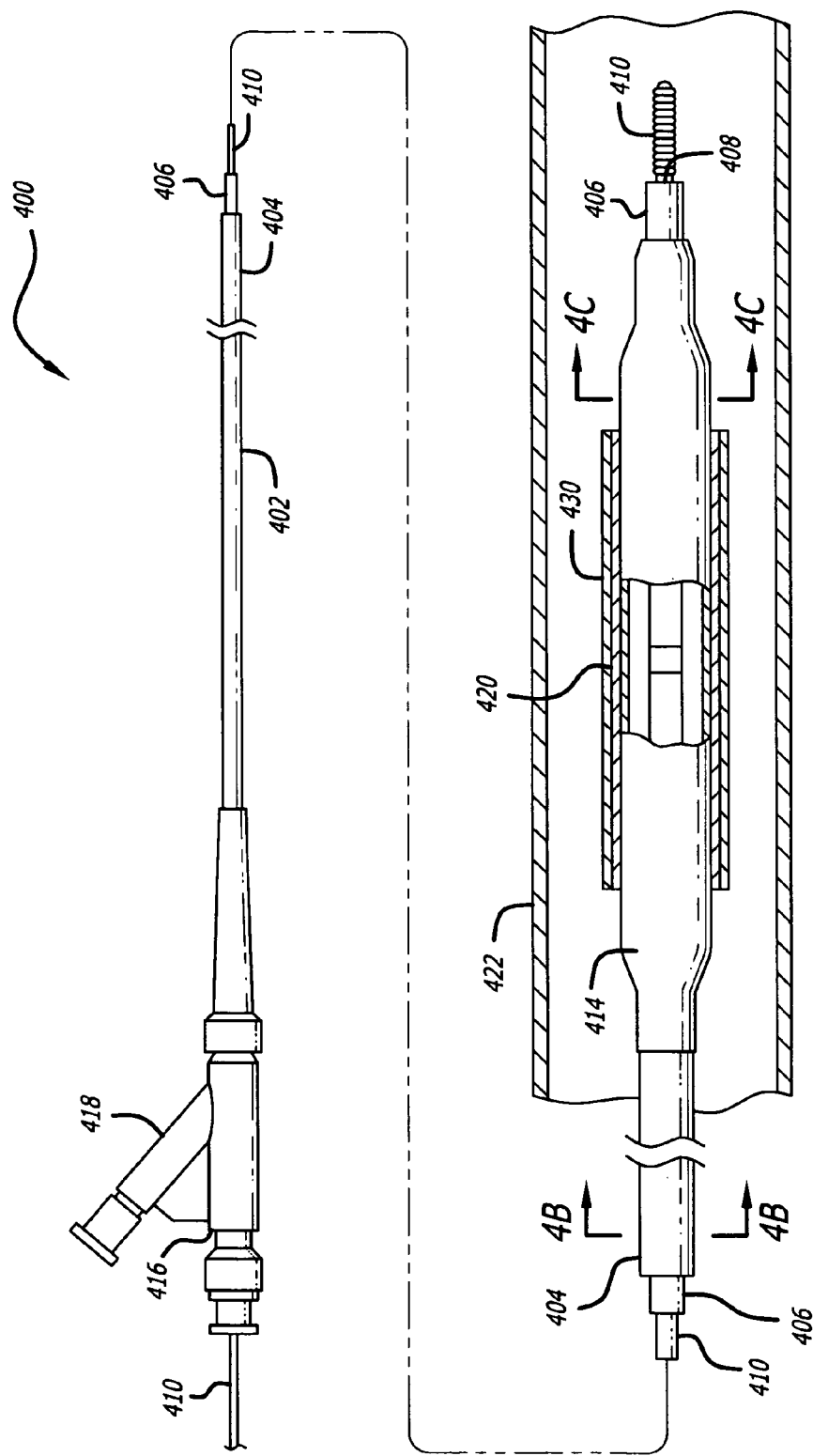
FIG. 4A illustrates an elevational view, partially in section, of a delivery system having a covered stent on a catheter balloon which may be used pursuant to methods of the present invention.
Figure 4B:
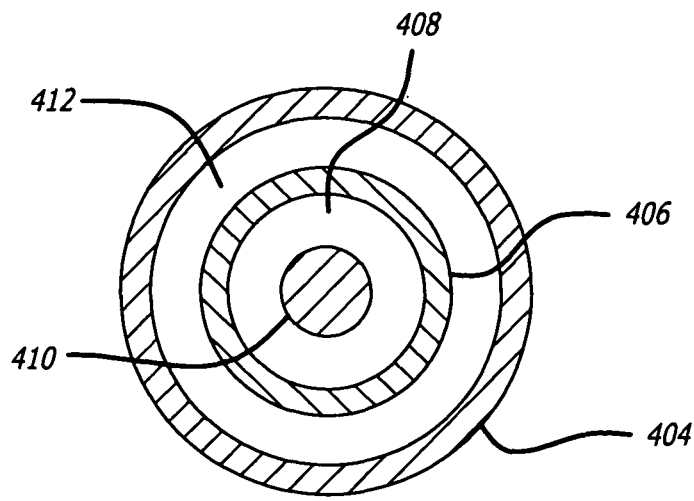
FIG. 4B is a cross-section of the delivery system of FIG. 4A taken at line 2-2.
Figure 4C:
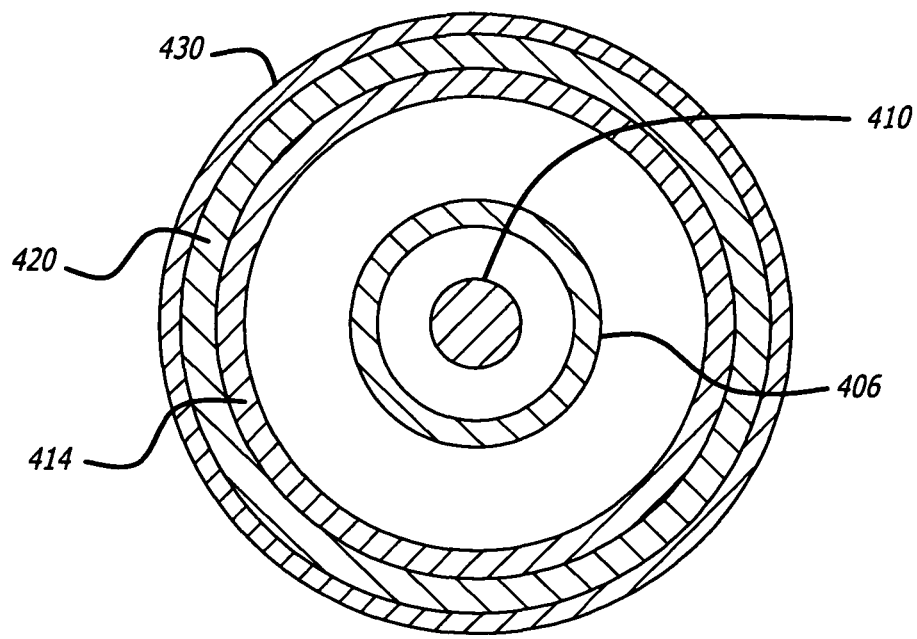
FIG. 4C is a cross-section of the delivery system of FIG. 4B taken at line 3-3.

FIGS. 4A-4C illustrate an over-the-wire type stent delivery balloon catheter 400 which can be used pursuant to embodiments of the present invention. Catheter 400 generally comprises an elongated catheter shaft 402 having an outer tubular member 404 and an inner tubular member 406. Inner tubular member 406 defines a guidewire lumen 408 adapted to slidingly receive a guidewire 410. The coaxial relationship between outer tubular member 404 and inner tubular member 406 defines annular inflation lumen 412 (see FIGS. 4B and 4C, illustrating transverse cross sections of the catheter 400 of FIG. 4A, taken along lines 2-2 and 3-3 respectively). An inflatable balloon 414 is disposed on a distal section of catheter shaft 402, having a proximal shaft section sealingly secured to the distal end of outer tubular member 404 and a distal shaft section sealingly secured to the distal end of inner tubular member 406, so that its interior is in fluid communication with inflation lumen 412. An adapter 416 at the proximal end of catheter shaft 402 is configured to direct inflation fluid through arm 418 into inflation lumen 412 and to provide access to guidewire lumen 408. Balloon 414 has an inflatable working length located between tapered sections of the balloon, with an expandable stent 420 mounted on the balloon working length. FIG. 4A illustrates the balloon 414 in an uninflated configuration prior to deployment of the stent 420. The distal end of catheter may be advanced to a desired region of a patient's body lumen 422 in a conventional manner, and balloon 414 inflated to expand stent 420, seating the stent in the body lumen 422. A stent cover 430 is on an outer surface of the stent 420. Stent cover 430 generally comprises a tubular body, which preferably conforms to a surface of the stent and expands with the stent during implantation thereof in the patient. Although stent cover 430 is illustrated on an outer surface of the stent 430 in FIG. 4A, the stent cover may be provided on all or part of an inner and/or an outer surface of the stent 420.

It should be appreciated that, in some embodiments, a self-expanding stent may be delivered by a stent delivery catheter without (or with) a balloon. Various methods are employed for delivery and implantation of a self-expanding stent. For instance, a self-expanding stent may be positioned at the distal end of a catheter around a core lumen. Self-expanding stents are typically held in an unexpanded state during delivery using a variety of methods including sheaths or sleeves which cover all or a portion of the stent. When the stent is in its desired location of the targeted vessel the sheath or sleeve is retracted to expose the stent which then self-expands upon retraction.

In some methods, a stent according to the present invention may be delivered to a tracheobronchial region by a stent delivery catheter (with or without a balloon) for treatment thereof.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. An implantable medical device comprising:
   a bioabsorbable tracheobronchial stent adapted to be positioned in a tracheobronchial passageway from a throat to lungs of a mammal, wherein the tracheobronchial stent is operable to hold open the tracheobronchial passageway from the throat to the lungs, the tracheobronchial stent having a generally tubular body comprising a single coiled fiber, the generally tubular body having a proximal concentric end region, a middle concentric region, and a distal concentric end region, wherein the proximal and distal concentric end regions each have a greater pitch and a greater pitch angle than a pitch and the pitch angle of the middle concentric region, wherein the pitch angle of the proximal and distal concentric end regions is between 50 degrees and 90 degrees and the pitch angle of the middle concentric region is 25 degrees to 70 degrees when the tracheobronchial stent is in a same state, and wherein an outer diameter of the middle concentric region is dimensioned to hold open the tracheobronchial passageway; and
   a first treatment agent and a second treatment agent disposed at least one of on and within at least a portion of the tracheobronchial stent, wherein the first and second treatment agents are subjected to controlled release, and wherein the first treatment agent is operable to treat mucous plugging and the second treatment agent is operable to treat granulation tissue formation.

2. The implantable medical device of claim 1, further comprising an anti-inflammatory disposed at least one of on and within at least a portion of the tracheobronchial stent.

3. The implantable medical device of claim 1, wherein the proximal and distal concentric end regions have greater pitch than the middle concentric region.

4. The implantable medical device of claim 1, further comprising a third treatment agent at least one of on and within the stent, in which the third treatment agent comprises at least one selected from an anti-mitotic, an anti-proliferative and an anti-migratory.

5. The implantable medical device of claim 1, wherein the implantable medical device is operable to be implanted within the tracheobronchial passageway.

6. An implantable medical device comprising:
   a bioabsorbable tracheobronchial stent adapted to be positioned in a tracheobronchial passageway from a throat to lungs of a mammal, wherein the bioabsorbable tracheobronchial stent is operable to hold open the tracheobronchial passageway from the throat to the lungs, and has a generally tubular body comprising a single coiled fiber, the generally tubular body having a proximal concentric end region, a middle concentric region, and a distal concentric end region, wherein the middle concentric region is operable to hold open the tracheobronchial passageway, and wherein the proximal and distal concentric end regions have a pitch angle of between 50 degrees and 90 degrees and the middle concentric region has a pitch angle of 25 degrees to 70 degrees when the tracheobronchial stent is in a radially expanded state, a pitch and the pitch angle of the proximal concentric end region and the distal concentric end region are greater than a pitch and the pitch angle of the middle concentric region; and a first treatment agent and a second treatment agent each disposed at least one of on and within at least a portion of the tracheobronchial stent, wherein the first and second treatment agents (a) are subjected to controlled release and (b) the first treatment agent is to treat mucous plugging and the second treatment agent is to treat granulation tissue formation.

7. The implantable medical device of claim 6, wherein the first treatment agent is combined with a polymer matrix forming a mixture, and wherein the mixture is coated on at least one of an abluminal surface and a luminal surface of the tracheobronchial stent.

8. The implantable medical device of claim 7, wherein the polymer matrix comprises a polymer that is selected from the group consisting of polyglycolide, polylactide, and copolymers and combinations thereof.

9. The implantable medical device of claim 6, wherein the first treatment agent is incorporated within the body of the tracheobronchial stent.

10. The implantable medical device of claim 6, wherein the bioabsorbable tracheobronchial stent comprises a material selected from the group consisting of polylactide, polyglycolide, polycaprolactones, and copolymers and combinations thereof.

11. The implantable medical device of claim 6, further comprising a treatment agent that is an anti-inflammatory.

12. The implantable medical device of claim 11, wherein the anti-inflammatory is selected from the group consisting of prednisone, oxymetholone, oxandrolone, methanodrostenolone, ibuprofen, diclofenac, diflunisal, fenoprofen, aspirin, sulindac, naproxen, indomethacin, piroxicam, ketoprofen, tolmetin and azapropazonelast.

13. The implantable medical device of claim 6, wherein the controlled release is from about 2 to about 24 months.

14. The implantable medical device of claim 6, wherein the tracheobronchial stent is balloon expandable or self-expandable.

15. The implantable medical device of claim 6, further comprising a treatment agent to treat inflammation.

16. The implantable medical device of claim 6, further comprising a third treatment agent at least one of on and within the stent, in which the third treatment agent comprises at least one selected from an anti-mitotic, an anti-proliferative and an anti-migratory.

17. The implantable medical device of claim 6, wherein the implantable medical device is operable to be implanted within the tracheobronchial passageway.

* * * * *